United States Patent
Stensrud (10) Patent No.: US 9,326,964 B2
(45) Date of Patent: May 3, 2016

(54) SEMI-SOLID COMPOSITIONS AND PHARMACEUTICAL PRODUCTS

(71) Applicant: PHOTOCURE ASA, Oslo (NO)

(72) Inventor: Gry Stensrud, Nittedal (NO)

(73) Assignee: PHOTOCURE ASA, Oslo (NO)

( * ) Notice: Subject to any disclaimer, the term of this patent is extended or adjusted under 35 U.S.C. 154(b) by 0 days.

(21) Appl. No.: 14/707,639

(22) Filed: May 8, 2015

(65) Prior Publication Data

US 2015/0238457 A1    Aug. 27, 2015

Related U.S. Application Data

(63) Continuation of application No. 13/377,722, filed as application No. PCT/EP2010/003532 on Jun. 11, 2010.

(30) Foreign Application Priority Data

Jun. 11, 2009   (EP) .................................... 09251537

(51) Int. Cl.

| | | |
|---|---|---|
| A61K 31/195 | (2006.01) | |
| A61K 31/221 | (2006.01) | |
| A61K 9/00 | (2006.01) | |
| A61K 9/06 | (2006.01) | |
| A61K 41/00 | (2006.01) | |
| A61K 47/10 | (2006.01) | |
| A61K 47/12 | (2006.01) | |
| A61K 47/14 | (2006.01) | |
| A61K 47/24 | (2006.01) | |
| A61K 47/26 | (2006.01) | |

(52) U.S. Cl.
CPC ............. *A61K 31/221* (2013.01); *A61K 9/0031* (2013.01); *A61K 9/0034* (2013.01); *A61K 9/06* (2013.01); *A61K 31/195* (2013.01); *A61K 41/0061* (2013.01); *A61K 47/10* (2013.01); *A61K 47/12* (2013.01); *A61K 47/14* (2013.01); *A61K 47/24* (2013.01); *A61K 47/26* (2013.01)

(58) Field of Classification Search
CPC .. A61K 9/0031; A61K 9/0034; A61K 31/195
USPC .................................................. 514/55, 463
See application file for complete search history.

(56) References Cited

U.S. PATENT DOCUMENTS

| | | | |
|---|---|---|---|
| 6,034,267 A * | 3/2000 | Gierskcky et al. ............ 560/155 | |
| 7,264,629 B2 | 9/2007 | Simkin et al. | |
| 2002/0132035 A1 | 9/2002 | Tamarkin et al. | |
| 2003/0125388 A1 | 7/2003 | Gander et al. | |
| 2004/0029855 A1 | 2/2004 | Klaveness et al. | |
| 2008/0096857 A1* | 4/2008 | Curaudeau et al. ........... 514/185 | |
| 2008/0227757 A1 | 9/2008 | Muller-Goymann et al. | |

FOREIGN PATENT DOCUMENTS

| | | |
|---|---|---|
| CN | 1460099 A | 12/2003 |
| EP | 0 704 209 A1 | 4/1996 |
| JP | 2003526637 A | 9/2003 |
| JP | 2004-505040 A | 2/2004 |
| JP | 2004-505105 A | 2/2004 |
| WO | 95/05813 A1 | 3/1995 |
| WO | 96-28412 A1 | 9/1996 |
| WO | 02-10120 A1 | 2/2002 |
| WO | 0209690 A2 | 2/2002 |
| WO | 03-011265 A2 | 2/2003 |
| WO | 03-041673 A2 | 5/2003 |
| WO | 2005-092838 A1 | 10/2005 |
| WO | 2006-051269 A1 | 5/2006 |
| WO | 2008/084241 A2 | 7/2008 |
| WO | 2009/074811 A2 | 6/2009 |
| WO | 2010/078929 A1 | 7/2010 |

OTHER PUBLICATIONS

Susan Barclay-Nichols; title: Better crafting through chemistry: Stearic acid; on-line article posted on Jul. 7, 2009. downloaded from http://swiftcraftymonkey.blogspot.com/2009/07/better-crafting-through-chemistry.html on Aug. 10, 2015.*
Bunke et al. (2000) Journal of Pharmaceutical Sciences, vol. 89(10): 1335-1341.
Donnelly et al., Abstract, "A bioadhesive patch containing 5-aminolevulinic acid for photo-dynamic therapy of vulval pathologies," Science Proceedings of the British Pharmaceutical Conference; Harrogate, England, UK; Sep. 15-17, 2003, 20030915; 20030915-20030917, Pharmaceutical Press, Wallingford.
Gay et al., (2014) Arkivoc 2014(iii), 228-238.
Hillemans et al., Int. J. Cancer 81:34-38 (1999).
Loh, et al., (1993) British Journal of Cancer, vol. 68(1), 45-51.
Montiero et al., (1989) Arch. Biochem. Biophys. 271, 206-217.
Wang et al., Photodiagnosis and Photodynamic Therapy, Jan. 14, 2009, vol. 5, pp. 251-255.
Winkler et al., "The influence of topical formulations on the permeation of 5-aminolevulinic acid and its n-butyl ester through excised human stratum corneum," 2005, European Journal of Pharmaceutics and Biopharmaceutics, vol. 60, pp. 427-437.
Yang et al., "Application of nanoparticle in photodynamic diagnosis for colorectal cancer," NSTI Nanotech 2006, vol. 1, 2006.

(Continued)

*Primary Examiner* — Johann R Richter
*Assistant Examiner* — Yanzhi Zhang
(74) *Attorney, Agent, or Firm* — Kenyon & Kenyon LLP (57) ABSTRACT

This invention relates to semi-solid compositions and semi-solid pharmaceutical products for use in the photodynamic treatment (PDT) of cancer, pre-cancerous conditions and non-cancerous conditions in the female reproductive system, the anus and the penis, preferably for use in PDT of endometrial, cervical, vulvar, vaginal, anal and penile dysplasia and HPV infections of the uterus, cervix, the vulva, the vagina, the anus and the penis. The semi-solid compositions and pharmaceutical products comprise an active ingredient which is 5-aminolevulinic acid (5-ALA) or a precursor or derivative of 5-ALA or pharmaceutically acceptable salts thereof. The invention relates further to methods of PDT of cancer, pre-cancerous conditions and non-cancerous conditions in the female reproductive system, the anus and the penis, wherein said semi-solid compositions and pharmaceutical products are used.

39 Claims, 1 Drawing Sheet

(56) References Cited

OTHER PUBLICATIONS

Soergel et al., "Lasers in Surgery and Medicine," 2008, vol. 40, pp. 611-615.
Barnett et al., Int. J. Cancer 2003, vol. 103, pp. 829-832.
Bodner et al., Anticancer Res. 2003, vol. 23, No. 2C, pp. 1785-1788.
Photocure ASA, "Summary of Product Characteristics of Metvix," retrieved from the Internet, Jul. 20, 2006, 6 pages.

* cited by examiner

SEMI-SOLID COMPOSITIONS AND PHARMACEUTICAL PRODUCTS

CROSS-REFERENCE TO RELATED APPLICATIONS

This application is a continuation of and claims priority to U.S. patent application Ser. No. 13/377,722, filed on Dec. 12, 2011, which is the U.S. national stage under 35 U.S.C. §371 of PCT/EP2010/003532, filed on Jun. 11, 2010, which claims priority to EP 09251537.8, filed on Jun. 11, 2009, the entire contents of which applications are incorporated herein by reference.

This invention relates to semi-solid compositions and semi-solid pharmaceutical products for use in the photodynamic treatment (PDT) of cancer, pre-cancerous conditions and non-cancerous conditions in the female reproductive system, the anus and the penis, preferably for use in PDT of endometrial, cervical, vulvar, vaginal, anal and penile dysplasia and HPV infections of the uterus, cervix, the vulva, the vagina, the anus and the penis. The semi-solid compositions and pharmaceutical products comprise an active ingredient which is 5-aminolevulinic acid (5-ALA) or a precursor or derivative of 5-ALA or pharmaceutically acceptable salts thereof. The invention relates further to methods of PDT of cancer, pre-cancerous conditions and non-cancerous conditions in the female reproductive system, the anus and the penis, wherein said semi-solid compositions and pharmaceutical products are used.

Photodynamic treatment (PDT) is a relatively new technique for the treatment of pre-cancerous lesions, cancer and non-cancerous diseases. PDT involves the administration of a photosensitiser or a precursor thereof to an area of interest. The photosensitiser or precursor thereof is taken up into the cells, where a precursor of a photosensitiser is converted into a photosensitiser. Upon exposure of the area of interest to light, the photosensitiser is excited, usually from a ground singlet state to an excited singlet state. It then undergoes intersystem crossing to a longer-lived excited triplet state. One of the few chemical species present in tissue with a ground triplet state is molecular oxygen. When the photosensitiser and an oxygen molecule are in proximity, an energy transfer can take place that allows the photosensitiser to relax to its ground singlet state, and create an excited singlet state oxygen molecule. Singlet oxygen is a very aggressive chemical species and will very rapidly react with any nearby biomolecules. Ultimately, these destructive reactions will kill cells through apoptosis or necrosis, whereby for instance cancer cells are selectively killed. The mechanisms are still not fully understood, but studies suggest that the clinical result (i.e. the selectivity for cancerous cells) is not due to selective uptake by cancerous cells. Rather, there are similar levels of uptake in all cell types, but the processes of conversion and elimination are different in malignant cells and generally in metabolically active cells, such as inflamed or infected cells, leading to a concentration gradient between cancerous and normal tissue.

Several photosensitisers are known and described in the literature including 5-aminolevulinic acid (5-ALA) and certain derivatives thereof, e.g. 5-ALA esters, which both are precursors of photosensitisers and which are converted to protoporphyrins, such as protoporphyrin IX (PpIX). Currently several pharmaceutical products comprising 5-ALA or an ester thereof are in clinical use for PDT. One of them is Metvix®, a dermal product in the form of a cream comprising 5-ALA methyl ester (developed by Photocure ASA, Norway and now sold by Galderma, Switzerland) for the photodynamic treatment of actinic keratosis and basal cell carcinoma. Another one is Levulan Kerastick® developed by DUSA Pharmaceuticals (Canada), a product for the photodynamic treatment of actinic keratosis which contains 5-ALA.

One of the most serious infections of the cervix is human papilloma virus (HPV) which can develop into cervical cancer. HPV infection is a common factor in the development of almost all cervical cancer cases. Estimates for the prevalence of HPV infections vary, but can typically be around 30% in all women. Recently, HPV vaccines have been developed such as Gardasil® and Cervarix®. However, cervical cancer remains a life-threatening disease. The cancer is unfortunately often diagnosed late since symptoms may be absent until the cancer has developed to a late stage. One possible early sign of cervical cancer is vaginal bleeding. Cervical cancer is diagnosed based on biopsy procedures. The main treatment is surgery, however, radiation and chemotherapy can be used in late stages of the disease. The prognosis of patients with cervical cancer depends on disease stage at the time of diagnosis. HPV infections may further affect the uterus, vulva, the vagina, the anus and the penis and these infections can develop into uterine cancer, vulvar cancer, vaginal cancer, anal cancer and penile cancer. Multiple infection sites such as vagina and cervix are possible.

Cervical intraepithelial neoplasia (CIN), also known as cervical dysplasia, is the potentially premalignant transformation and abnormal growth of squamous cells on the surface of the cervix. Corresponding thereto, endometrial intraepithelial neoplasia of the uterine lining (EIN), vulvar intraepithelial neoplasia (VIN), vaginal intraepithelial neoplasia (VAIN), anal intraepithelial neoplasia (AIN) and penile intraepithelial neoplasia (PeIN) also known as endometrial, vulvar, vaginal, anal and penile dysplasia, are the potentially premalignant transformation and abnormal growth of squamous cells on the uterine lining, in the vulva, the vagina (usually in the upper ⅓ of vagina, may be confluent with cervical lesions), the anus (on perianal skin or in the anal canal in flat mucosa) and on the surface of the penis. Most cases of such dysplasia remain stable, or are eliminated by the body's immune system without intervention. However a small percentage of cases progress to become cancer, usually squamous cell carcinoma (SCC), if left untreated. The major cause of CIN, EIN, VIN, VAIN, AIN and PeIN is chronic infection of the affected organs or tissue with HPV, especially the high-risk HPV types 16 or 18.

Over 100 types of HPV have been identified. About a dozen of these HPV types appear to cause cervical dysplasia and may lead to the development of cervical cancer. The earliest microscopic change corresponding to CIN is dysplasia of the epithelial or surface lining of the cervix, which is essentially undetectable by the woman. Cellular changes associated with HPV infection, such as koilocytes, are also commonly seen in CIN. CIN is usually discovered by a screening test, the Papanicolaou or "Pap" smear, by which also VIN and VAIN can be diagnosed. Anal pap smears exist to detect AIN. The purpose of these tests is to detect the changes early, while it has not yet progressed to invasive carcinoma, and is easier to cure. An abnormal Pap smear may lead to a recommendation for colposcopy of the cervix, vulva and vagina during which these organs and tissues are examined under magnification. Acetic acid solution or iodine solution may be applied to the surface to improve visualization of abnormal areas. Colposcopy can also be carried out on the penis. A biopsy is taken of any abnormal appearing areas and endometrial, cervical, vulvar, vaginal, anal and penile dysplasia can be diagnosed by histological examination of biopsy specimens.

Methods used to treat the above-mentioned intraepithelial neoplasia require removal or destruction of the surface cells of the cervix, vulva, vagina, anus and penis. These methods include excision, cryocautery, electrocautery, laser cautery, LEEP (cervix), and cervical conisation. All said methods may have side effects, like (cervical) stenosis with a resulting severe endometriosis, cervical insufficiency with premature delivery or low-birth weight babies and scarring and can include infections and hemorrhage. Hence there remains a medical need for methods of treatment of such intraepithelial neoplasia and PDT has proven to be an alternative with the treated patients showing good response rates.

In PDT of CIN, both 5-ALA and esters of 5-ALA have been used. K. Bodner et al., Anticancer Res 2003; 23 (2C): 1785-1788 used a solution of 5-ALA (12% w/v) in 0.9% aqueous NaCl solution containing 1% EDTA (w/v). The 5-ALA solution was prepared just before conducting the PDT. A. Barnett et al, Int. J. Cancer: 103, 829-832 (2003) have used a 3% or 5% (w/w) solution of 5-ALA in Intrasite Gel® which was prepared immediately prior to use. Intrasite Gel is a hydrogel comprising 2.3% of a modified carboxymethyl-cellulose (CMC) polymer together with propylene glycol (20%) as a humectant and preservative. P. Hillemanns et al., Int. J. Cancer: 81, 34-38 (1999) used 5-ALA hydrochloride which was freshly dissolved in sterile 0.9% aqueous NaCl solution at a final concentration of 20% (w/w) containing propylene glycol and adjusted at pH 5.5 using $NaHCO_3$. P. Soergel et al., Lasers in Surgery and Medicine 40:611-615, 2008 used 5-ALA hexyl ester which was applied in a thermo-gel formulation. As a thermogel base, Lutrol F-127, a bioadhesive poloxamer was used which was provided as a powder and the thermogel had to be prepared on site by adding sterile water. The 5-ALA hexyl ester containing thermogel had to be prepared freshly before application.

As seen above, freshly prepared formulations of 5-ALA and 5-ALA esters have been used for PDT of CIN, which is due to the limited stability of these compounds and which in turn limits the shelf life of pharmaceutical products in which they are present.

A number of different strategies have been adopted to try to overcome this problem. For instance, Metvix® containing 5-ALA methyl ester is stored in cold conditions. Levulan Kerastick® containing 5-ALA is sold as a 2-compartment formulation that is used to prepare a solution immediately before application. Hexvix® developed by Photocure ASA (Oslo, Norway), which comprises 5-ALA hexyl ester is in clinical use for photodynamic diagnosis (PDD) of bladder cancer and pre-cancerous lesions. In the PDD procedure, Hexvix is installed into the bladder in form of an aqueous solution which is freshly prepared on site from a lyophilized power of the 5-ALA hexyl ester and a dissolution medium.

These approaches, however, have disadvantages. For example, it is not always convenient to transport and store medicines in cold conditions. Moreover it is also generally preferable to provide pharmaceutical compositions in a ready-to-use form as these are most convenient for medical practitioners. Provision of ready-to-use forms also enables the compositions to be prepared with a reliable and accurate concentration. This is particularly important in the treatment of the majority of diseases including cancer where it can be critical that the correct and efficient dosage of therapeutic is administered.

US 2003/125388 describes an alternative approach to provide stable 5-ALA formulations wherein 5-ALA or a derivative thereof is dissolved or dispersed in a non-aqueous liquid having a dielectric constant of less than 80 at 25° C. and wherein said liquid stabilizes 5-ALA or a derivative thereof. It is hypothesized that the use of the non-aqueous liquid facilitates formation of the enol form of 5-ALA that then prevents its degradation. No stability data are shown though. Examples of suitable non-aqueous liquids mentioned in US 2003/125388 include glycerol and its mono-, di- and triesters with $C_1$-$C_{20}$ carboxylic acids, propylene glycol, alcohols, ethers, esters, poly(alkylene glycols), phospholipids, DMSO, N-vinylpyrrolidone and N,N-dimethyl acetamide. This composition may form part of a kit for therapeutic or diagnostic use. The other part of the kit is a composition comprising water. In this case the two parts of the kit are mixed prior to use. The approach in US 2003/125388 therefore suffers the same disadvantage as the Levulan Kerastick® in that it is generally undesirable to provide pharmaceutics in a form that requires the medical practitioner to formulate the pharmaceutical product that is actually administered.

Hence there is a need for alternative formulations of 5-ALA and 5-ALA esters and thus pharmaceutical products comprising 5-ALA and 5-ALA ester for use in PDT of in treating HPV infections of the cervix, the vulva, the vagina, the anus and the penis, cellular abnormalities in said organs or tissues, in particular cervical, vulvar, vaginal, anal and penile dysplasia.

WO 2009/074811 discloses solid pharmaceutical products for use in PDT of cancer and non-cancerous conditions like HPV infections in the female reproductive system, i.e. uterus, cervix and vagina. Said solid pharmaceutical products may be for administration in the form of a suppository or pessary. The term "solid" as defined in the application refers to the physical state of the entity being described, i.e. the pharmaceutical product, as being a solid rather than a liquid or gas. Liquids, solutions, gels and creams are not encompassed by said term. Said solid pharmaceutical products may be in the form of capsules, pellets, powders, tablets, granules, pills, suppositories, pessaries or mini-tablets said mini-tablets, powders, granules or pellets may further be provided within a capsule or compressed into a tablet.

We have now surprisingly found new and alternative semi-solid formulations comprising 5-ALA or a derivative thereof (e.g. an ALA ester) for use in the photodynamic treatment of cancer, pre-cancerous conditions and non-cancerous conditions in the female reproductive system, the anus and the penis, preferably for use in PDT of cervical, vulvar, vaginal, anal and penile dysplasia and HPV infections of the cervix, the vulva, the vagina, the anus and the penis.

The new solid formulations are stable at room temperature, are easy to handle for the health personnel and provide more convenience for the patients. They can further be readily applied to the cervix, vulva, vagina, anus and penis. Hence they overcome the above-mentioned disadvantages of the prior art and are capable of providing an effective concentration of 5-ALA or derivatives thereof at the intended site, and may also provide a substantially homogenous (i.e. uniform) distribution of 5-ALA or a derivative thereof (e.g. an ALA ester) at said intended site.

Thus, viewed from a first aspect the invention provides a semi-solid pharmaceutical product for use in the photodynamic treatment of cancer, pre-cancerous conditions and non-cancerous conditions in the female reproductive system, the anus and the penis comprising a) an active ingredient selected from 5-ALA, a precursor of 5-ALA or a derivative of 5-ALA and pharmaceutically acceptable salts thereof;

b) one or more triglycerides; and c) optionally one or more viscosity enhancers.

The term "semi-solid" denotes a physical state which is neither solid nor liquid. Semi-solids (or quasi-solids) are similar to a solid in some respects, e.g. a semi-solid can support its own weight and hold its shape but also shares some properties of liquids, such as shape conformity to something applying pressure to it, or the ability to flow under pressure. Semi-solids are characterized by a three-dimensional structure that is sufficient to impart solid-like character to the undisturbed system but that is easily broken down and realigned under an applied force. Semi-solids have a rigidity and viscosity intermediate between a solid and a liquid.

The term "pharmaceutical product" refers to the entity that is actually administered to a subject, e.g. a human or non-human animal, preferably a human.

The semi-semi-solid pharmaceutical products according to the inventions are creams, ointments, pastes and gels for topical application to the skin and to mucous membranes.

Creams are semi-solid emulsion systems with an opaque appearance. Their consistency and rheologic properties are based on whether the emulsion is o/w or w/o and on the nature of the solid in the internal phase. Ointments are composed mostly of fluid hydrocarbons meshed in a matrix of higher melting solid hydrocarbons. Pastes are basically ointments into which a high percentage of insoluble solids have been added. Gels are semi-solid systems in which a liquid phase is constrained within a three-dimensional polymeric matrix in which a high degree of physical cross-linking has been introduced.

The term "pre-cancerous condition" denotes a disease, syndrome, or finding that, if left untreated, may lead to cancer, e.g. dysplasia and neoplasia.

The term "non-cancerous conditions" include infections such as viral, bacterial or fungal infections, preferably HPV infection, or inflammation.

The term "female reproductive system" means the uterus, cervix, vagina and vulva, preferably the cervix, vagina and vulva.

The term "active ingredient" denotes 5-ALA and pharmaceutically acceptable salts thereof, precursors of 5-ALA and pharmaceutically acceptable salts thereof and derivatives of 5-ALA and pharmaceutically acceptable salts thereof.

The term "5-ALA" denotes 5-aminolevulinic acid, i.e. 5-amino-4-oxo-pentanoic acid.

The term "precursor of 5-ALA" denotes compounds which are converted metabolically to 5-ALA and are thus essentially equivalent thereto. Thus the term "precursor of 5-ALA" covers biological precursors for protoporphyrin in the metabolic pathway for haem biosynthesis.

The term "derivative of 5-ALA" includes chemically modified 5-ALA, for example esters.

The term "pharmaceutically acceptable salt" denotes a salt that is suitable for being used in the semi-solid pharmaceutical product and which fulfils the requirements related to for instance safety, bioavailability and tolerability (see for instance P. H. Stahl et al. (eds.) Handbook of Pharmaceutical Salts, Publisher Helvetica Chimica Acta, Zurich, 2002)

In a preferred embodiment, the semi-solid pharmaceutical products according to the invention are for use in photodynamic treatment of cervical, vaginal, vulvar, anal and penile dysplasia and HPV infections of the cervix, vagina, vulva, anus and penis.

The use of 5-ALA and derivatives thereof, e.g. 5-ALA esters in PDT and PDD is well known in the scientific and patent literature, see, for example, WO 2006/051269, WO 2005/092838, WO 03/011265, WO 02/09690, WO 02/10120, WO 2003/041673 and U.S. Pat. No. 6,034,267, the contents of which are incorporated herein by reference. All such derivatives of 5-ALA and their pharmaceutically acceptable salts are suitable for use in the methods herein described.

The synthesis of 5-ALA is known in the art. Further, 5-ALA and pharmaceutically acceptable salts thereof are commercially available, for instance from Sigma Aldrich.

The 5-ALA derivatives useful in accordance with the invention may be any derivative of 5-ALA capable of forming protoporphyrins, e.g. PpIX or a PpIX derivative in vivo. Typically, such derivatives will be a precursor of PpIX or of a PpIX derivative, e.g. a PpIX ester in the biosynthetic pathway for haem and which are therefore capable of inducing an accumulation of PpIX following administration in vivo. Suitable precursors of PpIX or PpIX derivatives include 5-ALA pro-drugs which might be able to form 5-ALA in vivo as an intermediate in the biosynthesis of PpIX or which may be converted, e.g. enzymatically, to porphyrins without forming 5-ALA as an intermediate. 5-ALA esters and pharmaceutically acceptable salts thereof, are among the preferred compounds for use in the invention described herein.

Esters of 5-ALA which are optionally N-substituted are preferred for use in the invention. Those compounds in which the 5-amino group is unsubstituted, i.e. 5-ALA esters, are particularly preferred. Such compounds are generally known and described in the literature see, for example, WO 96/28412 and WO 02/10120 to Photocure ASA, the contents of which are incorporated herein by reference.

Esters of 5-ALA with substituted or unsubstituted alkanols, i.e. alkyl esters and substituted alkyl esters, and pharmaceutically acceptable salts thereof, are especially preferred derivatives of 5-ALA for use in the invention. Examples of such compounds include those of general formula I and pharmaceutically acceptable salts thereof:

$$R^2{}_2N-CH_2COCH_2-CH_2CO-OR' \qquad (I)$$

wherein $R^1$ represents a substituted or unsubstituted alkyl group; and $R^2$ each independently represents a hydrogen atom or a group $R^1$ As used herein, the term "alkyl", unless stated otherwise, includes any long or short chain, cyclic, straight-chained or branched saturated or unsaturated aliphatic hydrocarbon group. Unsaturated alkyl groups may be mono- or polyunsaturated and include both alkenyl and alkynyl groups. Unless stated otherwise, such alkyl groups may contain up to 40 carbon atoms. However, alkyl groups containing up to 30 carbon atoms, preferably up to 10, particularly preferably up to 8, especially preferably up to 6 carbon atoms are preferred.

In compounds of formula I, the R' groups are substituted or unsubstituted alkyl groups. If $R^1$ is a substituted alkyl group, one or more substituents are either attached to the alkyl group and/or interrupt the alkyl group. Suitable substituents that are attached to the alkyl group are those selected from hydroxy, alkoxy, acyloxy, alkoxycarbonyloxy, amino, aryl, nitro, oxo, fluoro, $-SR_3$, $-NR^3{}_2$ and $-PR^3{}_2$, wherein $R^3$ is a hydrogen atom or a $C_{1-6}$ alkyl group. Suitable substituents that interrupt the alkyl group are those selected from $-O-$, $-NR_3-$, $-S-$ or $-PR_3$.

In a preferred embodiment, $R^1$ is an alkyl group substituted with one or more aryl substituents, i.e. aryl groups, preferably substituted with one aryl group.

As used herein, the term "aryl group" denotes an aromatic group which may or may not contain heteroatoms like nitrogen, oxygen or sulfur. Aryl groups which do not contain heteroatoms are preferred. Preferred aryl groups comprise up to 20 carbon atoms, more preferably up to 12 carbon atoms, for example, 10 or 6 carbon atoms. Preferred embodiments of aryl groups are phenyl and naphthyl, especially phenyl. Further, the aryl group may optionally be substituted by one or more, more preferably one or two, substituents. Preferably, the aryl group is substituted at the meta or para position, most preferably the para position. Suitable substituents include halo alkyl, e.g. trifluoromethyl, alkoxy, preferably alkoxy groups containing 1 to 6 carbon atoms, halo, e.g. iodo, bromo, chloro or fluoro, preferably chloro and fluoro, nitro and $C_{1-6}$ alkyl, preferably $C_{1-4}$ alkyl. Preferred $C_{1-6}$ alkyl groups include methyl, isopropyl and t-butyl, particularly methyl. Particularly preferred aryl substituents are chloro and nitro. However, still more preferably the aryl group is unsubstituted.

Preferred such aryl substituted $R^1$ groups are benzyl, 4-isopropylbenzyl, 4-methylbenzyl, 2-methylbenzyl, 3-methylbenzyl, 4-[t-butyl]benzyl, 4-[trifluoromethyl]benzyl, 4-methoxybenzyl, 3,4-[di-chloro]benzyl, 4-chlorobenzyl, 4-fluorobenzyl, 2-fluorobenzyl, 3-fluorobenzyl, 2,3,4,5,6-pentafluorobenzyl, 3-nitrobenzyl, 4-nitrobenzyl, 2-phenylethyl, 4-phenylbutyl, 3-pyridinyl-methyl, 4-diphenyl-methyl and benzyl-5[(1-acetyloxyethoxy)-carbonyl]. More preferred such R1 groups are benzyl, 4-isopropylbenzyl, 4-methylbenzyl 4-nitrobenzyl and 4-chlorobenzyl. Most preferred is benzyl.

If $R^1$ is a substituted alkyl group, one or more oxo substituents are preferred. Preferably, such groups are straight-chained $C_{4-12}$ alkyl groups which are substituted by one or more oxo groups, preferably by one to five oxo groups. The oxo groups are preferably present in the substituted alkyl group in an alternating order, i.e. resulting in short polyethylene glycol substituents. Preferred examples of such groups include 3,6-dioxa-1-octyl and 3,6,9-trioxa-1-decyl.

If $R^1$ is an unsubstituted alkyl group, R' groups that are saturated straight-chained or branched alkyl groups are preferred. If R' is a saturated straight-chained alkyl group, $C_{1-10}$ straight-chained alkyl group are preferred. Representative examples of suitable straight-chained alkyl groups include methyl, ethyl, n-propyl, n-butyl, n-pentyl, n-hexyl and n-octyl. Particularly preferred are $C_{1-6}$ straight-chained alkyl group, most particularly preferred are methyl and n-hexyl. If $R^1$ is a saturated branched alkyl group, such branched alkyl groups preferably consist of a stem of 4 to 8, preferably 5 to 8 straight-chained carbon atoms and said stem is branched by one or more $C_{1-6}$ alkyl groups, preferably $C_{1-2}$ alkyl groups. Examples of such saturated branched alkyl groups include 2-methylpentyl, 4-methylpentyl, 1-ethylbutyl and 3,3-dimethyl-1-butyl.

In compounds of formula I, each $R^2$ independently represents a hydrogen atom or a group $R^1$. Particularly preferred for use in the invention are those compounds of formula I in which at least one $R^2$ represents a hydrogen atom. In especially preferred compounds each $R^2$ represents a hydrogen atom.

Preferably, compounds of formula I and pharmaceutically acceptable salts thereof and used in the semi-solid pharmaceutical product of the invention, wherein $R^1$ is methyl or hexyl, more preferably n-hexyl and both $R^2$ represent hydrogen, i.e. 5-ALA methyl ester, 5-ALA hexyl ester and pharmaceutically acceptable salts thereof, preferably the HCl salts. The preferred compound for use in the semi-solid pharmaceutical product of the invention is 5-ALA hexyl ester and pharmaceutically acceptable salts thereof, preferably the HCl salt or sulfonic acid salts or sulfonic acid derivative salts.

5-ALA esters and pharmaceutically acceptable salts thereof for use in the invention may be prepared by any conventional procedure available in the art, e.g. as described in WO 96/28412 and WO 02/10120. Briefly, 5-ALA esters may be prepared by reaction of 5-ALA with the appropriate alcohol in the presence of a catalyst, e.g. an acid. Pharmaceutically acceptable salts of 5-ALA esters may be prepared as described before by reaction of a pharmaceutically acceptable 5-ALA salt, e.g. 5-ALA hydrochloride with the appropriate alcohol. Alternatively compounds for use in the invention like 5-ALA methyl ester or 5-ALA hexyl ester may be available commercially, e.g. from Photocure ASA, Norway.

The 5-ALA esters for use in the invention may be in the form of a free amine, e.g. —$NH_2$, —$NHR^2$ or —$NR^2R^2$ or preferably in the form of a pharmaceutically acceptable salt. Such salts preferably are acid addition salts with pharmaceutically acceptable organic or inorganic acids. Suitable acids include, for example, hydrochloric, nitric, hydrobromic, phosphoric, sulfuric, sulfonic and sulfonic acid derivatives, the latter are described in WO2005/092838 to Photocure ASA, the entire contents of which are incorporated herein by reference. A preferred acid is hydrochloride acid, HCl, sulfonic acid and sulfonic acid derivatives. Procedures for salt formation are conventional in the art.

Thus, in a preferred embodiment, the invention provides a semi-semi-solid pharmaceutical product for use in the photodynamic treatment of cancer, pre-cancerous conditions and non-cancerous conditions in the female reproductive system, the anus and the penis comprising
  a) a derivative of 5-ALA or a pharmaceutically acceptable salt thereof, preferably a 5-ALA ester or a pharmaceutically acceptable salt thereof;
  b) one or more triglycerides; and
  c) optionally one or more viscosity enhancers.

In a preferred embodiment, said 5-ALA ester is a compound of formula (I) or an pharmaceutically acceptable salt thereof, wherein $R^1$ represents an unsubstituted alkyl group, preferably an unsubstituted saturated straight-chained or branched alkyl group, more preferably an unsubstituted saturated straight-chained $C_{1-10}$ alkyl group. More preferably, said 5-ALA ester is 5-ALA hexyl ester and in a further preferred embodiment, said pharmaceutically acceptable salt of 5-ALA hexyl ester is the HCl salt or a sulfonic acid salt or sulfonic acid derivative salt, such as mesylate, tosylate or napsylate.

The compounds a) hereinbefore described may be used for the manufacture of the semi-solid pharmaceutical product according to the invention in any conventional manner. The desired concentration of 5-ALA or derivative of 5-ALA or precursor of 5-ALA in the pharmaceutical products of the invention will vary depending on several factors including the nature of the compound, the nature and form of the product in which this is presented and the intended site and mode of administration. Generally, however, the concentration of 5-ALA or derivative of 5-ALA or precursor of 5-ALA or pharmaceutically acceptable salts thereof is conveniently in the range 0.25 to 50%, preferably 0.5 to 30%, e.g. 0.5 to 15%, preferably 1 to 10% and more preferably 1 to 7% by weight of the total weight of the semi-solid pharmaceutical product.

The semi-solid pharmaceutical products according to the invention comprise one or compounds b), one or more triglycerides (triacylglycerols). A triglyceride is comprised of one molecule glycerol and 3 fatty acid molecules. The 3 fatty acids may be identical or different fatty acids. The compounds b) are vehicles and/or carriers.

The triglycerides used in the invention are liquid or semi-solid at room temperature, i.e. at temperatures of about 18° C. to about 25° C. If the triglycerides are liquid at room temperature, it is preferred to add one or more viscosity enhancers c) to obtain a semi-solid product. If the triglycerides are semi-solid at room temperature, one or more viscosity enhancers c) may or may not be added.

Further, the triglycerides should be inert compounds, i.e. compounds which do not react with the active ingredient a) or which promote degradation of the active ingredient.

The triglycerides may be synthetic, semi-synthetic or of animal and/or vegetable origin. The triglycerides may be pure/isolated triglycerides or a part of a mixture, such as a mixture of triglycerides, monoglycerides and/or diglycerides and/or free fatty acids and/or unsaponifiable lipids. Such mixtures are typically found edible oils of animal and/or vegetable origin. If the triglycerides are part of a mixture, they preferably constitute the major part of said mixture. In the following, such mixtures are also denoted "triglycerides".

Since the triglycerides are used in the pharmaceutical product according to the invention, which is for use in a human or non-human animal, they need to be of pharmaceutical grade and fulfill the requirements and standards of such products with regard to physiological acceptance, tolerability and safety.

The term "one or more triglycerides" means that the semi-solid pharmaceutical product according to the invention contains one triglyceride or several different triglycerides. By way of example, the semi-solid pharmaceutical product may contain tricaprylin (caprylic acid triglyceride) or tricaprylin and caprylic/capric triglyceride. Further, by way of example the semi-solid pharmaceutical product may contain soybean oil, which is a mixture of triglycerides of alpha-linolenic acid, linoleic acid, oleic acid, stearic acid and palmitic acid.

Preferred liquid triglycerides are selected from edible oils of animal and/or vegetable origin and/or fractions thereof, such as soybean oil, palm kernel oil, corn oil, olive oil, almond oil, safflower oil, peanut oil, coconut oil, sunflower oil, castor oil or pine oil Other examples of liquid triglycerides include hydrogenated or preferably partially hydrogenated triglycerides selected from partially or fully hydrogenated soybean oil, rapeseed oil, sunflower oil, coconut oil and fractions thereof. The liquid triglycerides oil may be synthetic or semi-synthetic, such as medium-chain triglycerides (MCT).

Preferred semi-solid triglycerides are selected from edible semi-solid fats of animal and/or vegetable origin and/or fractions thereof, such as palm oil, cottonseed oil or lard. Other examples of semi-solid triglycerides include hydrogenated or partially hydrogenated triglycerides selected from partially or fully hydrogenated soybean oil, rapeseed oil, sunflower oil, coconut oil and fractions thereof.

In a preferred embodiment, the triglyceride is a triglyceride of glycerol and 3 identical or different $C_2$-$C_{22}$ fatty acids, more preferably 3 identical or different $C_4$-$C_{18}$ fatty acids, even more preferably 3 identical or different $C_6$-$C_{18}$ fatty acids and most preferably 3 identical or different $C_6$-$C_{12}$ fatty acids. In a more preferred embodiment, the triglyceride is a triglyceride of glycerol and 3 identical $C_2$-$C_{22}$ fatty acids, more preferably 3 identical $C_4$-$C_{18}$ fatty acids, even more preferably 3 identical $C_6$-$C_{18}$ fatty acids and most preferably 3 identical $C_6$-$C_{12}$ fatty acids.

Most preferred triglycerides are tricaprylin, tricaproin, triheptanoin, caprylic/capric triglyceride and caprylic/capric/linoleic triglyceride and caprylic/capric/succinic triglyceride. Some of these triglycerides are marketed under the name "Miglyol®", e.g. with Miglyol 812 being caprylic/capric triglyceride, Miglyol 818 being caprylic/capric/linoleic triglyceride and Miglyol 808 being tricaprylin. A manufacturer or such triglycerides is for instance Sasol, Witten, Germany.

In a preferred embodiment, the semi-solid pharmaceutical product according to the invention comprises as compound b) one or more triglycerides selected from tricaprylin, tricaproin, triheptanoin, caprylic/capric triglyceride, caprylic/capric/linoleic triglyceride and caprylic/capric/succinic triglyceride.

The triglycerides used in the invention may be prepared using standard processes and procedures well-known in the art, although many are commercially available from various manufacturers such like Sasol, Croda, Gattefossé and others.

The compounds b) are vehicles or carriers in the semi-solid pharmaceutical products of the invention and thus are present in relatively high concentrations. The concentration compounds b) is conveniently in the range of about 50 to 98%, preferably 60 to 96% and more preferably of 65 to 94% by weight of the total weight of the semi-solid pharmaceutical product. If compound c) is not present, the concentration of compounds b) is conveniently in the range of about 50 to 99.75%, preferably 70 to 99.5%, e.g. 85 to 99.5%, more preferably 90 to 99% and most preferably 93 to 99%.

The semi-solid pharmaceutical products according to the invention further optionally comprise one or more compounds c), i.e. one or more viscosity enhancers.

The term "viscosity enhancer" denotes a compound that thickens or stiffens a mixture of compounds b) and the active ingredient a). If a liquid compound b) is used, a mixture of compound b) and the active ingredient a) is a liquid, e.g. a solution or a suspension, and by adding one or more compounds c), the mixture will become semi-solid.

Generally, any viscosity enhancer which—upon being added to a mixture of compounds b) and the active ingredient a)—results in said mixture becoming a semi-solid may be used. Further, the viscosity enhancer should be an inert compound, i.e. a compound which does not react with the active ingredient or which does not promote degradation of the active ingredient. Usually, the viscosity enhancer will be chosen according to the nature of the active ingredient and the nature of the compound b), i.e. the triglyceride carrier or vehicle.

The term "one or more viscosity enhancers" means that the semi-solid pharmaceutical product according to the invention may contain one viscosity or several different viscosity enhancers. By way of example, the semi-solid pharmaceutical product may contain stearyl alcohol or stearic acid. Further, by way of example the semi-solid pharmaceutical product may contain cetostearyl alcohol, which is a mixture of fatty alcohols, consisting predominantly of cetyl and stearyl alcohols or may contain stearyl alcohol and stearic acid.

Examples of viscosity enhancers are cellulose and derivatives thereof like carboxymethylcellulose sodium, hydroxyethylcellulose (HEC), hydroxypropyl methylcellulose (HPMC), methylcellulose (MC), synthetic polymers like polyacrylic acid (carbomer), polyethylene glycols, vegetable gums like guar gum, gum arabic or tragacanth, starch and starch derivatives, carrageenan, agar, gelatin, wax and waxy solids.

In a more preferred embodiment, the viscosity enhancer is a hydrophobic compound, more preferably a wax or a waxy solid, most preferably a solid fatty alcohol or solid fatty acid. In a more preferred embodiment, said wax or waxy solid has a melting point between about 45° C. and 75° C. Preferred examples of such viscosity enhancers are beeswax, yellow wax, white beeswax, carnauba wax, castor wax, cetyl alcohol, stearyl alcohol, cetostearyl alcohol (cetearyl alcohol), arachidyl alcohol, behenyl alcohol, palmitic acid or stearic acid.

Some of the mentioned viscosity enhancers such as some fatty alcohols do also exhibit emulsifying properties.

The above mentioned viscosity enhancers are commercially available compounds and are manufactured and supplied by various suppliers, e.g. Sasol (Witten, Germany) International Specialty Products (New Jersey, USA) BASF (Ludwigshafen, Germany), Croda (USA).

The viscosity enhancer is present in an amount which is necessary to obtain a semi-solid product. The actual amount will depend on the nature of the mixture of the active ingredient a) and the one or more triglycerides b), e.g. its viscosity and also on the nature of the one or more viscosity enhancers. If one or more a semi-solid triglycerides are used in to manufacture the semi-solid pharmaceutical product according to the invention, the addition of a viscosity enhancer may not be necessary at all. The amount and the nature of the one or more viscosity enhancers impacts the drop point of the semi-solid pharmaceutical product according to the invention, a drop point well above the body temperature would limit the spreading of the product to the surface of the tissue or organ to be treated and thus negatively impact the bioavailability of the active ingredient. If the semi-solid pharmaceutical product is for use in humans, the drop point of the product is preferably in the range of 28 to 43° C., more preferably in the range of 41 to 32° C. The drop point is defined and determined as described in European Pharmacopoeia 6.0 section 2.2.17: the drop point is the temperature at which the first drop of melting substance to be examined falls from a cup under defined conditions.

In a preferred embodiment, the semi-solid pharmaceutical product according to the invention comprises one or more liquid triglycerides and one or more viscosity enhancers are present. In a more preferred embodiment, said one or more liquid triglycerides are triglyceride of glycerols and 3 identical or different $C_2$-$C_{22}$ fatty acids, more preferably 3 identical or different $C_4$-$C_{18}$ fatty acids, even more preferably 3 identical or different $C_6$-$C_{18}$ fatty acids and most preferably 3 identical or different $C_6$-$C_{12}$ fatty acids. In a more preferred embodiment, the triglyceride is a triglyceride of glycerol and 3 identical $C_2$-$C_{22}$ fatty acids, more preferably 3 identical $C_4$-$C_{18}$ fatty acids, even more preferably 3 identical $C_6$-$C_{18}$ fatty acids and most preferably 3 identical $C_6$-$C_{12}$ fatty acids. In another more preferred embodiment, the semi-solid pharmaceutical product according to the invention comprises said aforementioned one or more liquid triglycerides and one or more viscosity enhancers selected from a wax or a waxy solid, most preferably selected from a solid fatty alcohol or solid fatty acid.

Generally, if one or more viscosity enhancers are present in the semi-solid pharmaceutical product according to the invention, they are present in an amount of about 0.5 to 40%, preferably 1 to 30% by weight of the total weight of the semi-solid pharmaceutical product.

The semi-solid pharmaceutical product further comprises
d) optionally one or more emulsifiers
e) optionally one or more mucoadhesive
f) optionally one or more pharmaceutically acceptable excipients other than b) and c)
g) optionally one or more surface penetration agents; and
h) optionally one or more chelating agents.

The semi-solid pharmaceutical product according to the invention optionally comprises one or more emulsifiers.

An emulsifier also known as a surfactant, surface active material or emulgent is a substance which stabilizes an emulsion. A wide variety of emulsifiers are used in pharmacy to prepare emulsions.

The term "one or more emulsifier" means that the semi-solid pharmaceutical product according to the invention contains one emulsifier or several different emulsifiers.

In a preferred embodiment, emulsifiers are non-ionic emulsifiers.

Preferred non-ionic emulsifiers are selected from the group of short chain partial glycerides, i.e. esters of glycerol with short chain fatty acids, whereby only a part of the existing hydroxyl groups are esterified, i.e. mono- or diglycerides or mixtures of mono- and diglycerides. Preferred partial glycerides are mono- or diglycerides or mixtures of mono- and diglycerides of $C_6$-$C_{10}$ fatty acids.

Yet other preferred non-ionic emulsifiers are esters of glycerol with fatty acids and alpha-hydroxy acids, for instance glyceryl stearate citrate, glyceryl citrate/lactate/oleate/linoleate, glyceryl cocoate/citrate/lactate and glyceryl isostearate.

Yet other preferred non-ionic emulsifiers are fatty alcohols and/or ethoxylated fatty alcohols like cetostearyl alcohol or cetomacrogol.

Yet other preferred non-ionic emulsifiers are ethoxylated fatty acids, like ethoxylated castor oil.

Yet other preferred non-ionic emulsifiers are non-ethoxylated and ethoxylated esters of sorbitan and fatty acids, sold under the name "Span" and "Tween", i.e. polysorbates, preferably (polyoxyethylene) sorbitan monolaurate, (polyoxyethylene) sorbitan monopalmitate, (polyoxyethylene) sorbitan monostearate, (polyoxyethylene) sorbitan monooleate, (polyoxyethylene) sorbitan tristearate or (polyoxyethylene) sorbitan trioleate.

Yet other preferred non-ionic emulsifiers are lecithins, e.g. egg yolk lecithin or soybean lecithin or phospholipids derived from lecithin, preferably phosphatidylcholine.

Yet other preferred non-ionic emulsifiers are polyethylene glycol based compounds like polyethylene glycol 400 monostearate.

Yet other preferred non-ionic emulsifiers are ethoxylated glycerides, like ethoxylated caprylocaproyl glyceride or products obtained from the reaction of polyethylene glycol and natural or hydrogenated oils, such as palm kernel oil, hydrogenated palm kernel oil, castor oil, hydrogenated castor oil, almond oil, apricot kernel oil and the like.

These preferred emulsifiers of the latter non-ionic emulsifiers are lauroyl macrogol-32 glyceride, Gelucire® 44/14 (Gattefossé); stearoyl macrogol glyceride, Gelucire® 50/13 (Gattefossé); PEG-50 castor oil, Emalex C-50 (Nihon Emulsion); Eumulgin® HRE 40 (Cognis); PEG-45 hydrogenated castor oil, PEG-8 caprylic/capric glycerides, Labrasol® (Gattefossé); either alone or in a mixture with other emulsifiers.

Yet other more preferred non-ionic emulsifiers are poloxamers, i.e. triblock copolymers composed of a central hydrophobic chain of polyoxypropylene flanked by two hydrophilic chains of polyoxyethylene. Poloxamers are also known by the trade name Pluronics®. Most preferred poloxamers are those which are liquid and have a pH below 7, preferably below 6 such as Pluronic® L43 or Pluronic® L44, either alone or in a mixture with other emulsifiers, preferably other poloxamers such as Pluronic® F68.

If the active ingredient a) is a $C_1$-$C_{10}$ alkyl ester of 5-ALA or a pharmaceutically acceptable salt thereof, preferably non-ionic emulsifiers with high hydrophilic-lipophilic balance values (HLB values) are used, even more preferably with a HLB value of at least 7, preferably with a HLB value of at least 12, more preferably with an HLB value of about 12-18. If more than one emulsifier is used, it is also possible to use an emulsifier with an HLB value below 7 or above 18, provided that the resulting mixture of emulsifiers has a HLB value of at least 7 and preferably a HLB value of about 12-18.

Generally, the emulsifier is present in the semi-solid pharmaceutical product in an amount necessary to promote uniform distribution of the pharmaceutical product at the site of use, e.g. in the vagina in the anus. Usually, the emulsifier, if present, is present in an amount of 0.5 to 15%, preferably 1 to 10%, more preferably 2 to 8% by weight of the total weight of the semi-solid pharmaceutical product.

Emulsifiers which may optionally be used in the invention may be prepared using standard processes and procedures well-known in the art, although many are available commercially from various manufacturers such like Sasol, Croda, Cognis, Gattefossé, American Lecithin Company, BASF, Cytec and others.

The semi-solid pharmaceutical product according to the invention optionally comprises one or more mucoadhesives, i.e. one mucoadhesive or several different mucoadhesives.

The term "mucoadhesive" denotes a compound which exhibits an affinity for a mucosa surface, i.e. adhere to that surface through the formation of bonds which are generally non-covalent in nature, whether binding occurs through interaction with the mucous and/or the underlying cells. In the context of the invention, the mucosa surface is a mucosa surface of the uterus, cervix, vagina, vulva, anus and penis. Preferably, one or more mucoadhesives are optionally added to semi-solid pharmaceutical products which are intended for use on the uterus or cervix or in the vagina and anus.

The mucoadhesive which is optionally present in the semi-solid pharmaceutical product of the invention is preferably a mucoadhesive compound that is not degraded by the acidic environment and the presence of lactic acid in the vagina nor metabolized by bacterial and non-bacterial enzymes present in the female reproductive system, in particular in the vagina and the cervix.

Mucoadhesives which may be used in the semi-solid pharmaceutical products of the invention may be natural or synthetic compounds, polyanionic, polycationic or neutral, water-soluble or water-insoluble, but are preferably large, e.g. having a molecular weight of 500 kDa to 3000 kDa, e.g. 1000 kDa to 2000 kDa, water-insoluble cross-linked, e.g. containing 0.05% to 2% cross-linker by weight of the total polymer, prior to any hydration, water-swellable polymers capable of forming hydrogen bonds. Preferably such mucoadhesive compounds have a mucoadhesive force greater than 100, especially preferably greater than 120, particularly greater than 150, expressed as a percent relative to a standard in vitro, as assessed according to the method of Smart et al., 1984, J. Pharm. Pharmacol., 36, pp 295-299.

Preferred mucoadhesive compounds are selected from polysaccharides, preferably dextran, pectin, amylopectin or agar; gums, preferably guar gum or locust bean gum; salts of alginic acid, preferably sodium alginate or magnesium alginate; poly(acrylic acid) and crosslinked or non-crosslinked copolymers of poly(acrylic acid) and derivatives of poly (acrylic acid) such as salts and esters like for instance carbomer (carbopol).

Some of the aforementioned viscosity enhancers present in the semi-solid pharmaceutical composition also have mucoadhesive properties and if such viscosity enhancers are used, additional mucoadhesives may not be needed or desired.

When present, the mucoadhesives may conveniently be provided in a concentration range of 0.05 to 30% by weight of the total weight of the pharmaceutical product in which it is present, e.g. about 1 to 25% by weight of the total weight of the pharmaceutical product in which it is present.

The semi-solid pharmaceutical product according to the invention optionally comprises one or more pharmaceutically acceptable excipients which are different from the excipients b), c) and the optional excipient d). Such optional one or more pharmaceutically acceptable excipients may be selected from the group of antiadherents, fillers, binders, colors, odor enhancers, glidants, lubricants, disintegrants, spreading agents, solvents or preservatives. The skilled man will be able to select suitable excipients based on their purpose. Common excipients that may be used in the pharmaceutical products herein described are listed in various handbooks (e.g. D. E. Bugay and W. P. Findlay (Eds) Pharmaceutical excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe fair Pharmazie, Kosmetik and angrenzende Gebiete (Edition Cantor Aulendorf, 1989)).

If the semi-solid pharmaceutical product according to the invention optionally comprises one or more pharmaceutically acceptable solvents, such solvents may be a free fatty acid, a free fatty alcohol, an aqueous solution, e.g. a buffer, or water. However, it is preferred that the semi-solid pharmaceutical product according to the invention does not contain any water, i.e. is water-free. By water-free, it is meant that no water is added to the semi-solid pharmaceutical product and that any measurable water content of the product is due to water possibly contained in any of the ingredients a)-h).

The semi-solid pharmaceutical product according to the invention optionally comprises one or more surface penetration assisting agents. Such agents may have a beneficial effect in enhancing the photosensitizing effect the active ingredient, i.e. of 5-ALA, the derivative of 5-ALA or the precursor of 5-ALA present in the pharmaceutical products of the invention.

Surface penetration assisting agents, especially dialkylsulphoxides such as dimethylsulphoxide (DMSO) may therefore be included in the products. The surface penetration assisting agent may be any of the penetration assisting agents described in the pharmaceutical literature, e.g. chelators (e.g. EDTA), surfactants (e.g. sodium dodecyl sulfate), non-surfactants, bile salts (sodium deoxycholate), fatty alcohols e.g. oleylalcohol, fatty acids e.g. oleic acid and esters of fatty acids and alcohol, e.g. isopropylmyristate. Examples of surface penetration assisting agents include isopropanol, 1-[2-(decylthio)ethyl]-azacyclopentan-2-one (HPE-101 available from Hisamitsu), DMSO and other dialkylsulphoxides, in particular n-decylmethyl sulphoxide (NDMS), dimethylsulphacetamide, dimethylformamide (DMFA), dimethylacetamide, isopropylmyristate, oleylalcohol and oleic acid, various pyrrolidone derivatives (Woodford et al., J. Toxicol. Cut. & Ocular Toxicology, 1986, 5: 167-177) and Azone® (Stoughton et al., Drug Dpv. Ind. Pharm. 1983, 9: 725-744) or mixtures thereof.

The use of glycols such as propylene glycol as surface penetration assisting agents is not recommended since it may promote the degradation of the active ingredient a) in the semi-solid pharmaceutical product according to the invention.

When present, the surface penetration assisting agent may conveniently be provided in a concentration range of 0.2 to 20% by weight of the total weight of the pharmaceutical product in which it is present, e.g. about 1 to 15% and preferably 0.5 to 10% by weight of the total weight of the pharmaceutical product in which it is present.

The semi-solid pharmaceutical product according to the invention optionally comprises one or more chelating agents. Such agents may also have a beneficial effect in enhancing the photosensitizing effect of 5-ALA, the derivative of 5-ALA or the precursor of 5-ALA present in the pharmaceutical products of the invention.

Chelating agents may, for example, be included in order to enhance the accumulation of PpIX since the chelation of iron by the chelating agent prevents its incorporation into PpIX to form haem by the action of the enzyme ferrochelatase, thereby leading to a build up of PpIX. The photosensitizing effect is therefore enhanced.

Suitable chelating agents that may be included in the semi-solid pharmaceutical product aminopolycarboxylic acids, such as any of the chelants described in the literature for metal detoxification or for the chelation of paramagnetic metal ions in magnetic resonance imaging contrast agents. Particular mention may be made of EDTA, CDTA (cyclohexane tri-amine tetraacetic acid), DTPA and DOTA and well known derivatives and analogues thereof. EDTA and DTPA are particularly preferred. Other suitable chelating agents are desferrioxamine and siderophores and they may be used alone or in conjunction with aminopolycarboxylic acid chelating agents such as EDTA.

Some of the above-mentioned chelating agents do also exhibit surface penetration assisting agent properties, e.g. EDTA.

Where present, the chelating agent may conveniently be used at a concentration of 0.01 to 12%, e.g. 0.1 to 10% by weight based on the composition in which it is present.

The semi-solid pharmaceutical products of the invention are formulated as a cream, an ointment, a paste or a gel. Conventional and known methods may be used to prepare such creams, ointments, pastes and gels. Mixture of the compounds a) and b) and optionally c) to h) may be promoted by methods known in the art, e.g. stirring, optionally along with heating the mixture. Generally, compounds c) to h), if present, and the one or more triglycerides are mixed during stirring and optionally heating until a homogenous mixture, preferably fluid, is achieved. If the mixture is heated, the temperature is decreased while stirring and the active ingredient a) is added during cooling and stirring at a temperature of about 40° C. or below. The stirring of the final product is continued until room temperature is reached.

An advantage of the semi-solid pharmaceutical products of the invention is that they are stable. In particular, the active ingredients present within the pharmaceutical products of the invention are not prone to degradation and/or decomposition. As a result, the pharmaceutical products can be stored, e.g. at or below room temperature and ambient humidity, preferably at room temperature and ambient humidity for at least 6 months, more preferably at least 12 months, still more preferably at least 24 months or more, e.g. up to 36 months.

The semi-solid pharmaceutical products according to the invention are preferably viscous or to a certain degree viscous at the patient's body temperature. This makes the product easy to handle, e.g. the product may be easily administered to the female reproductive system, the anus or the penis without becoming immediately low viscous or liquid upon rise of temperature from room temperature to body temperature. It further ensures that the pharmaceutical product remains at the site of administration, i.e. on the surface of the uterus, cervix, vagina, vulva, anus or penis.

In one embodiment, the viscosity of the pharmaceutical product at the patient's body temperature is as such that no additional means like pessaries, diaphragms, caps, plugs, adhesive bandages or patches are needed for keeping the product at the site of administration for the desired time. This embodiment is preferred if the product is administered by a physician, e.g. gynecologist or andrologist, or a nurse and the patient is preferably under observation of a nurse, physician or other health personnel during incubation, i.e. in the time period between administration and light treatment.

In another embodiment, the viscosity the pharmaceutical product at room temperature is as such that it is preferred to apply it to pessaries, diaphragms, caps, adhesive bandages or patches which are placed at the site of treatment ensuring that the product remains at those sites of administration.

In a preferred embodiment, the semi-solid pharmaceutical products according to the invention are for use in photodynamic treatment of dysplasia and HPV infections in the female reproductive system, the anus and the penis, more preferably endometrial, cervical, vaginal, vulvar, anal and penile dysplasia and HPV infections of the uterus, cervix, vagina, vulva, anus and penis. In a more preferred embodiment, the semi-solid pharmaceutical products according to the invention are for use in photodynamic treatment of endometrial, cervical, vaginal and vulvar dysplasia and HPV infections in the uterus, cervix, vagina and vulva. In a most preferred embodiment, the semi-solid pharmaceutical products according to the invention are for use in photodynamic treatment of cervical and vaginal dysplasia and HPV infections in cervix and vagina.

In said most preferred embodiments, it is preferred to use a device which is adapted to receive an effective amount, i.e. dose of semi-solid pharmaceutical products according to the invention. The preferred device is body shaped to allow full and secure insertion into the vagina. The preferred device further comprises irradiation means, i.e. a light source which is suitable to irradiate light suitable for photoactivation, i.e. to achieve the desired photodynamic effect. In a preferred embodiment, said device is inserted by a physician or nurse into the vagina and placed at the desired site (vagina, cervix) where it stays during incubation and photodynamic treatment. A timer may be part of said preferred device which, after being activated before the device is inserted, ensures that irradiation starts after the desired incubation period and continues for a determined light treatment period. In a more preferred embodiment, the device is disposable and adapted to be removed by the patient without the need to see her physician again. Such devices, e.g. caps or rod-shaped devices, are described in the international patent application number PCT/EP2009/009037 by Photocure ASA and are preferably used in combination with the semi-solid pharmaceutical products according to the invention.

After administration of the pharmaceutical product to the site to be treated, said site is exposed to light to achieve the desired photoactivation and photodynamic treatment. The length of time period between administration and exposure to light (incubation time) will depend on the nature of the active ingredient and the nature of the pharmaceutical product. Generally, it is necessary that the active ingredient within said pharmaceutical product is converted into a photosensitiser and achieves an effective tissue concentration at the site of treatment prior to photoactivation. The incubation time is about 30 min to 10 hours, preferably 1 hour to 7 hours, e.g. 3 hours to 5 hours.

The irradiation will generally be applied for a short time with a high light intensity, i.e. a high fluence rate or for a longer time with a low light intensity, i.e. low fluence rate. The latter is preferred for a PDT procedure wherein the semi-solid pharmaceutical product is applied to pessaries, diaphragms, caps, adhesive bandages or patches, e.g. to a device as described in the international patent application number PCT/EP2009/009037. If for instance cancer, pre-cancerous conditions and non-cancerous conditions in the female reproductive system are treated, such a device, e.g. a cap, can be filled with the semi-solid pharmaceutical product according to the invention which is placed at the site of treatment, e.g. the cervix. The device is hardly noticed by the patient since it is fully inserted in the body. After an incubation time to allow the built-up of protoporphyrins, the device will automatically start emitting irradiation. Again since the patient hardly notices the device, the light treatment can be carried out at a low fluence rate over a longer time period, e.g. at a fluence rate of 1-10 mW/cm$^2$ over a time period of several hours. This is beneficial both in terms of reduced discomfort to the patient and in the efficacy of the treatment.

Generally, suitable light sources are lasers, lamps and preferably LED lamps. The energy consumption per unit time of the lamp or laser system should be such that the heating of tissue does not result in discomfort or damage to the patient. The irradiation will in general be applied at a dose level of 10 to 200 Joules/cm$^2$, for example at 50 Joules/cm$^2$. The lamp or laser system is therefore preferably arranged to provide, in operation, a light intensity in the range of 0.5-100 mW/cm$^2$, and most preferably in the range of 1-10 mW/cm$^2$.

The wavelength of light used for irradiation may be selected to achieve an efficacious photodynamic effect. Light having wavelengths of between 300-800 nm, for example, the range 400-700 nm has been found to be particularly effective. It can be particularly important to include the wavelengths 630 and 690 nm. Red light (600-670 nm) is particularly preferred since light at this wavelength is known to penetrate well into tissue. Therefore preferably the lamp or laser emits, in use, light having wavelengths of between 630-690 nm. In some embodiments the laser or lamp system comprises filters to ensure that only light within a certain wavelength range, such as those mentioned above, is emitted. Alternatively, the treatment surface of a device as mentioned above may be designed such that only light having these preferred wavelengths is transmitted.

A single irradiation may be used or alternatively a light split those is delivered in a number of fractions, e.g. a few to several minutes between irradiations, may be used. Multiple irradiations may also be applied but are not preferred.

Treatment of the patient is preferably carried out with a single dose of the semi-solid pharmaceutical product. However, if treatment is not complete, it can be repeated.

The semi-solid pharmaceutical products according to the invention may be provided separately (e.g. in a tube or jar) or already contained in a drug delivery system, e.g. pessaries, diaphragms, caps, adhesive bandages or patches or a device, e.g. a cap, as described in the international patent application number PCT/EP2009/009037.

Alternatively, the semi-solid pharmaceutical products according to the invention may be provided in the form of a kit comprising the pharmaceutical product and a drug delivery system.

The disclosed semi-solid pharmaceutical products and method for photodynamic therapy may be combined with other therapeutic procedures, for example administration of other therapeutic drugs. These therapeutic drugs might be administered to the patient prior, together or subsequent to the semi-solid pharmaceutical products. Other routes of administration may be oral, intravascular or dermal. Typical such drugs include hormones, antibacterial agents, antifungal agents, antiviral agents, anticancer agents or combination of such drugs.

In a second aspect, the invention provides the use of
a) an active ingredient selected from 5-ALA, a precursor of 5-ALA or a derivative of 5-ALA and pharmaceutically acceptable salts thereof;
b) one or more triglycerides; and
c) optionally one or more viscosity enhancers in the manufacture of a semi-solid pharmaceutical product or semi-solid composition for use in the photodynamic treatment of cancer, pre-cancerous conditions and non-cancerous conditions in the female reproductive system, the anus and the penis.

In a third aspect the invention provides a method of photodynamic treatment of cancer, pre-cancerous conditions and non-cancerous conditions in the female reproductive system, the anus and the penis, said method comprising the steps of:
(a) administering to a subject, preferably a human subject a semi-solid pharmaceutical product or a semi-solid composition according to the invention;
(b) waiting for a time period necessary for the active ingredient within said pharmaceutical product to be converted into a photosensitiser and achieve an effective tissue concentration at the desired site; and
(c) photoactivating the photosensitiser.

In a fourth aspect the invention provides a semi-solid pharmaceutical product or a semi-solid composition contained in a drug delivery system for use in the photodynamic treatment of cancer, pre-cancerous conditions and non-cancerous conditions in the female reproductive system, the anus and the penis, comprising, in case of the semi-solid pharmaceutical composition or containing, in case of the semi-solid compositions
a) an active ingredient selected from 5-ALA, a precursor of 5-ALA or a derivative of 5-ALA and pharmaceutically acceptable salts thereof;
b) one or more triglycerides; and
c) optionally one or more viscosity enhancers.

In a preferred embodiment, said drug delivery system is selected from pessaries, diaphragms, caps, adhesive bandages or patches or a device, e.g. a cap, as described in the international patent application number PCT/EP2009/009037.

In a fifth aspect the invention provides a kit comprising
(i) a semi-solid pharmaceutical product or a semi-solid composition for use in the photodynamic treatment of cancer, pre-cancerous conditions and non-cancerous conditions in the female reproductive system, the anus and the penis comprising, in case of the semi-solid pharmaceutical composition or containing, in case of the semi-solid compositions:
a) an active ingredient selected from 5-ALA, a precursor of 5-ALA or a derivative of 5-ALA and pharmaceutically acceptable salts thereof;
b) one or more triglycerides; and
c) optionally one or more viscosity enhancers; and
(ii) a drug delivery device.

In a preferred embodiment, said drug delivery device is selected from pessaries, diaphragms, caps, adhesive bandages or patches or a device, e.g. a cap, as described in the international patent application number PCT/EP2009/009037.

Some of the semi-solid pharmaceutical products are novel compositions and hence in a sixth aspect, the invention provides semi-solid compositions consisting of
a) an active ingredient selected from 5-ALA, a precursor of 5-ALA or a derivative of 5-ALA and pharmaceutically acceptable salts thereof;
b) one or more triglycerides; and
c) optionally one or more viscosity enhancers.

The preferred embodiments of the semi-solid compositions are identical with the preferred embodiments of the semi-solid pharmaceutical products described earlier, i.e. the preferred compounds a), b) and optionally c) and preferred combinations thereof, also described earlier.

Preferably, the semi-solid compositions according the invention are those wherein the active ingredient is a derivative of 5-ALA, preferably a 5-ALA ester or a pharmaceutically acceptable salt thereof, the one or more triglycerides is a liquid triglyceride, preferably selected from triglycerides of glycerol and 3 identical or different $C_2$-$C_{22}$ fatty acids, more preferably 3 identical or different $C_4$-$C_{18}$ fatty acids, even more preferably 3 identical or different $C_6$-$C_{18}$ fatty acids and most preferably 3 identical or different $C_6$-$C_{12}$ fatty acids and the one or more viscosity enhancers are present. In a more preferred embodiment, said one or more viscosity enhancers are selected from a wax or a waxy solid and more preferably selected from a solid fatty alcohol or solid fatty acid.

The semi-solid compositions according to the invention consist of:
a) 0.25 to 50%, preferably 0.5 to 30%, e.g. 0.5 to 15%, preferably 1 to 10% and more preferably 1 to 7% by weight of the total weight of the semi-solid composition, and, if compound c) is not present
b) 50 to 99.75%, preferably 70 to 99.5%, e.g. 85 to 99.5%, more preferably 90 to 99% and most preferably 93 to 99% by weight of the total weight of the semi-solid composition.

If compound c) is present, the concentration of compounds b) is conveniently in the range of about 50 to 98%, preferably 60 to 96% and more preferably of 65 to 94% by weight of the total weight of the semi-solid composition.

In a seventh aspect the invention provides the semi solid composition according to the invention for use as a medicament.

In an eighth aspect, the invention provides the semi solid composition according to the invention for use in photodynamic treatment of dysplasia and HPV infections in the female reproductive system, the anus and the penis, more preferably endometrial, cervical, vaginal, vulvar, anal and penile dysplasia and HPV infections of the uterus, cervix, vagina, vulva, anus and penis. In a more preferred embodiment, the semi-solid compositions according to the invention are for use in photodynamic treatment of endometrial, cervical, vaginal and vulvar dysplasia and HPV infections in the uterus, cervix, vagina and vulva. In a most preferred embodiment, the semi-solid compositions according to the invention are for use in photodynamic treatment of cervical and vaginal dysplasia and HPV infections in cervix and vagina.

EXAMPLE 1

Semi-Solid Compositions According to the Invention

Semi-solid compositions according to the invention were prepared as follows: caprylic/capric triglyceride (Miglyol® 812, Sasol, Witten) and compounds c) to h), if present, were mixed during stirring with an overhead stirrer (IKA RW 20n, IKA Werke, Germany) at a stirring rate of 240 rpm and heating to about 50° C. until a homogenous fluid was achieved. The temperature was allowed to decrease to about 40° C. while stirring, and n-hexyl aminolevulinic acid ester (HAL) hydrochloride (HAL HCl, Photocure, Norway) was added. The mixture was homogenized at 17500 rpm for 1.5 min for optimum mixing. Thereafter, the mixture was allowed to cool down to room temperature (about 21° C.) under further stirring. Stirring was continued manually using a spatula in case the mixture became too viscous to be stirred by the overhead stirrer.

The drop point of the prepared products was determined as described in European Pharmacopoeia 6.0 section 2.2.17. The numbers in the tables below represent % by weight of the total product.

The following compounds were used in the compositions:
a) HAL HCl: active ingredient
b) caprylic/capric triglyceride: triglyceride
c) stearic acid (Mallinckrodt), cetostearyl alcohol (Cognis): viscosity enhancer
d) polysorbat 80 (Croda), polysorbat 60 (Croda), sorbitan stearate (Uniqema), sorbitan trioleate (ICI): emulsifier
f) dimeticon (Sikema): spreading agent; oleyl alcohol (Zelmic), isopropyl myristate (Croda): solvent
g) polypropylene glycol (Albion): surface penetration assisting agent

| | 1 | 2 | 3 | 4 | 5 | 6 | 7 | 8 | 9 |
|---|---|---|---|---|---|---|---|---|---|
| HAL HCl | 1 | 1 | 5 | 1 | 1 | 1 | 1 | 1 | 1 |
| Miglyol ® 812 | 69 | 75 | 75 | 70 | 70 | 70 | 70 | 70 | 60 |
| Stearic acid | 30 | 24 | 20 | 27 | 27 | 27 | 27 | 27 | 29 |
| Cetostearyl alcohol | — | — | — | — | — | — | — | — | — |
| Polysorbat 80 | — | — | — | 2 | — | — | — | — | — |
| Polysorbat 60 | — | — | — | — | 2 | — | — | — | — |
| Sorbitan stearate | — | — | — | — | — | 2 | — | — | — |
| Sorbitan trioleate | — | — | — | — | — | — | 2 | — | — |
| Dimeticon | — | — | — | — | — | — | — | 2 | — |
| Propylene glycol | — | — | — | — | — | — | — | — | 10 |
| Oleyl alcohol | — | — | — | — | — | — | — | — | — |
| Isopropyl myristate | — | — | — | — | — | — | — | — | — |
| Drop point (° C.) | 41 | 39 | 37 | 40 | 41 | 40 | 41 | 41 | 38 |

| | 10 | 11 | 12 | 13 | 14 | 15 | 16 | 17 | 18 |
|---|---|---|---|---|---|---|---|---|---|
| HAL HCl | 1 | 1 | 1 | 1 | 1 | 1 | 1 | 1 | 1 |
| Miglyol ® 812 | 65 | 65 | 70 | 70 | 70 | 70 | 70 | 70 | 70 |
| Stearic acid | 29 | 29 | — | 14 | 24 | 19 | 22 | 22 | 15 |
| Cetostearyl alcohol | — | — | 29 | 15 | 5 | 10 | — | — | 7 |
| Polysorbat 80 | — | — | — | — | — | — | 2 | — | 2 |
| Polysorbat 60 | — | — | — | — | — | — | — | — | — |
| Sorbitan stearate | — | — | — | — | — | — | — | 2 | — |
| Sorbitan trioleate | — | — | — | — | — | — | — | — | — |
| Dimeticon | — | — | — | — | — | — | — | — | — |
| Propylene glycol | — | — | — | — | — | — | 5 | — | 5 |
| Oleyl alcohol | 5 | — | — | — | — | — | — | — | — |
| Isopropyl myristate | — | 5 | — | — | — | — | — | 5 | — |
| Drop point (° C.) | 42 | 42 | 39 | 32 | 40 | 33 | 36 | 40 | 25 |

| | 19 | 20 | 21 | 22 | 23 | 24 | 25 | 26 | 27 |
|---|---|---|---|---|---|---|---|---|---|
| HAL HCl | 1 | 1 | 1 | 1 | 1 | 1 | 1 | 1 | 1 |
| Miglyol ® 812 | 70 | 70 | 65 | 65 | 65 | 67 | 60 | 68 | 65 |
| Stearic acid | 22 | 21 | 19 | 19 | 22 | 24 | 24 | 23 | 22 |
| Cetostearyl alcohol | — | — | 7 | 5 | 4 | — | 5 | — | 4 |
| Polysorbat 80 | — | 2 | 2 | — | 2 | 2 | — | 2 | 2 |
| Polysorbat 60 | — | — | — | — | — | — | — | — | — |
| Sorbitan stearate | — | — | — | — | — | — | — | — | — |
| Sorbitan trioleate | 2 | 1 | 1 | — | 1 | — | 1 | 1 | 1 |
| Dimeticon | — | — | — | — | — | — | — | — | — |
| Propylene glycol | — | 5 | 5 | 10 | 5 | 5 | 10 | 5 | 5 |
| Oleyl alcohol | — | — | — | — | — | — | — | — | — |
| Isopropyl myristate | 5 | — | — | — | — | — | — | — | — |
| Drop point (° C.) | 39 | 33 | 31 | 33 | 35 | 37 | 35 | 36 | 34 |

|  | 28 | 29 | 30 | 31 | 32 | 33 |
|---|---|---|---|---|---|---|
| HAL HCl | 5 | 1 | 5 | 5 | 5 | 5 |
| Miglyol ® 812 | 62 | 65 | 77 | 65 | 60 | 64 |
| Stearic acid | 21 | 24 | 18 | 22 | 23 | 21 |
| Cetostearyl alcohol | 4 | — | — | — | 4 | — |
| Polysorbat 80 | 2 | — | — | 2 | 2 | — |
| Polysorbat 60 | — | — | — | — | — | — |
| Sorbitan stearate | — | — | — | — | — | — |
| Sorbitan trioleate | 1 | — | — | 1 | 1 | — |
| Dimeticon | — | — | — | — | — | — |
| Propylene glycol | 5 | 10 | — | 5 | 5 | 10 |
| Oleyl alcohol | — | — | — | — | — | — |
| Isopropyl myristate | — | — | — | — | — | — |
| Drop point (° C.) | 31 | 37 | 39 | N/A | N/A | N/A |

EXAMPLE 2

Stability

Compositions 30, 31, 32 and 33 were prepared as described in Example 1. Immediately after preparation, the compositions were visually assessed and the HAL HCl content was determined by HPCL. 20 g of the freshly prepared compositions were transferred into clear glass containers (3 containers per compositions) with a screw lid. A glass container with each composition was stored for 2 month at 25° C./60% RH, 30° C./65% RH and 40° C./75% RH. 3 samples were taken from each glass container after 1 month and the HAL HCl content was determined by HPLC. The medium HAL HCl content was determined. In addition, the compositions were visually assessed.

Time Point 0

| Composition | HAL HCl (%) | Visual Assessment |
|---|---|---|
| 30 | 5.14 | Off white |
| 31 | 4.97 | Off white |
| 32 | 4.95 | Lighter than off white |
| 33 | 5.06 | Lighter than off white |

Time Point 1 Month

| Storage Condition | Composition | HAL HCl (%) | Visual Assessment |
|---|---|---|---|
|  | 30 |  |  |
| 25° C./60% RH |  | 5.20 | Off white |
| 30° C./65% RH |  | 5.12 | Off white |
| 40° C./75% RH |  | 5.79* | Two layers, top layer off white, bottom layer lighter than light yellow-brown |
|  | 31 |  |  |
| 25° C./60% RH |  | 4.20 | Off white |
| 30° C./65% RH |  | 3.61 | Darker than off white |
| 40° C./75% RH |  | 2.65 | Lighter than light yellow-brown |
|  | 32 |  |  |
| 25° C./60% RH |  | 4.20 | Darker than off white |
| 30° C./65% RH |  | 3.73 | Darker than off white |
| 40° C./75% RH |  | 2.67 | Light yellow-brown |
|  | 33 |  |  |
| 25° C./60% RH |  | 3.68 | Off white |
| 30° C./65% RH |  | 2.80 | Off white |
| 40° C./75% RH |  | 1.43 | Two layers, top layer off white, bottom layer lighter than light yellow-brown |

*higher values due to phase separation (drop point of composition 30 is below 40° C.)

Composition 30 which does not contain any propylene glycol displayed a better stability than the other propylene glycol containing compositions. Of the propylene glycol containing compositions, the two with the lowest propylene glycol content (compositions 31 and 32 containing 5% propylene glycol, respectively), displayed a relatively better stability than composition 33 containing 10% propylene glycol.

Composition 30 was chosen for a long term stability assessment: the composition was stored at 25° C./60% RH and 40° C./75% RH, respectively. Visual assessment and determination of HAL HCl was carried out as described above after 1, 2, 6 and 9 months, respectively.

| Time (months) | Storage Conditions | HAL HCl (%) | Visual Assessment |
|---|---|---|---|
| 0 |  | 5.14 | Off white |
| 1 | 25° C./60% RH | 5.20 | Off white |
| 1 | 40° C./75% RH | 5.79* | Phase separation, top layer off white, bottom layer lighter than light yellow-brown |
| 2 | 25° C./60% RH | 5.06 | Off white |
| 2 | 40° C./75% RH | 5.14 | Phase separation, light yellow-brown |
| 6 | 25° C./60% RH | 5.07 | Off white |
| 6 | 40° C./75% RH | 5.19 | Phase separation, top layer off white, bottom layer brownish oil with crystals |
| 9 | 25° C./60% RH | 5.30 | Off white |
| 9 | 40° C./75% RH |  | N/A |

*higher values due to phase separation (drop point of composition 30 is below 40° C.)

Composition 30 showed excellent stability at room temperature over an extended time period (9 months).

EXAMPLE 3

Comparison of stability

EXAMPLE 3a

Comparison of a Semi-Solid Composition According to the Invention and a Semi-Solid Composition Comprising Glycerol Instead of Compound b)

US 2003/125388 suggests formulations, e.g. water-free formulations of 5-ALA or a derivative thereof, in non-aqueous liquids having a dielectric constant of less than 80 at 25° C., which acts as stabilizer of 5-ALA or a derivative thereof. Such formulations are for instance suitable for the treatment of epithelial neoplasia of the vulva. Glycerol is disclosed as a preferred non-aqueous liquid. Glycerol has a dielectric constant of 42.5 at 25° C.

Semi-solid compositions A and B were prepared by dissolving/dispersing HAL HCl in glycerol (Speziol G pharma grade, Cognis, 99.8%) or in caprylic/capric triglyceride (Miglyol® 812, Sasol) and adding a viscosity enhancer.

Composition A was prepared by adding glycerol and HAL HCl to a glass beaker. The mixture was stirred with an overhead stirrer (IKA RW 20n, IKA Werke, Germany) at a stirring rate of 240 rpm-1000 rpm. 1-ethenyl-2-pyrrolidinone homopolymer (PVP) (Plasdone K85-95, ISP) was added as a viscosity enhancer slowly to avoid lump formation. Stirring was continued until a homogenous mixture was formed. A clear, thready gel was obtained. Composition B was prepared according to Example 1 with caprylic/capric triglyceride and stearic acid as viscosity enhancer. A white, grainy ointment was obtained. Compositions A* and B* were prepared as hereinbefore described, but without any HAL HCl. Composition A* was obtained as a clear thready gel, composition B* as a white, grainy ointment The numbers in table below represent % by weight of the total product.

|  | A | A* | B | B* |
|---|---|---|---|---|
| HAL HCl | 1 | — | 1 | — |
| Miglyol ® 812 | — | — | 69 | 70 |
| Stearic acid | — | — | 30 | 30 |
| Glycerol | 97 | 98 | — | — |
| Plasdone K85-95 | 2 | 2 | — | — |

Immediately after preparation, the compositions were visually assessed and the HAL HCl content of A and B was determined by HPCL. 5 g of the freshly prepared compositions were transferred into clear glass containers (3 containers per composition) with a screw lid. A glass container with each composition was stored for 1-6 months at 5° C./ambient RH, 25° C./60% RH and 40° C./75% RH. 3 samples were taken from each glass container after 1, 2, 3 and 6 months and the HAL HCl content was determined by HPLC. The medium HAL HCl content was determined. In addition, the compositions were visually assessed. The compositions A* and B* were stored at the same conditions, they were visually assessed after 1, 2, 3 and 6 months and they were used as a "blank" sample in the HPLC assay.

Composition A

|  | 5° C./ambient RH | | 25° C./60% RH | | 40° C./75% RH | |
|---|---|---|---|---|---|---|
| Months | HAL (%) | Visual Ass. | HAL (%) | Visual Ass. | HAL (%) | Visual Ass. |
| 0 | 0.97 | Beige clear | 0.97 | Beige clear | 0.97 | Beige clear |
| 1 | 0.98 | Clear | 0.97 | Clear | 0.91 | Clear |
| 2 | 0.99 | Clear | 0.98 | Clear | 0.89 | Clear |
| 3 | 0.98 | Clear | 0.96 | Clear, more viscous | 0.82 | Pale yellow clear |
| 6 | 0.97 | Clear | 0.92 | Clear, more viscous | 0.62 | Clear, more viscous |

Composition A* kept a clear appearance at all storage conditions.

Composition B:

|  | 5° C./ambient RH | | 25° C./60% RH | | 40° C./75% RH | |
|---|---|---|---|---|---|---|
| Months | HAL (%) | Visual Ass. | HAL (%) | Visual Ass. | HAL (%) | Visual Ass. |
| 0 | 1.00 | White, grainy | 1.00 | White, grainy | 1.00 | White, grainy |
| 1 | 1.01 | White, grainy | 0.98 | White, grainy | 1.02 | White, grainy |
| 2 | 1.03 | White, grainy | 1.03 | White, grainy | 1.00 | White, grainy |
| 3 | 1.00 | White, grainy | 0.99 | White, grainy | 0.95 | White, grainy |
| 6 | 0.94 | White, grainy | 0.99 | White, grainy | 0.85 | White, grainy |

Composition B* kept a white grainy appearance at all storage conditions.

While composition B was stable over a period of 6 months at 25° C., the HAL HCl concentration in composition A decreased considerably under these conditions with about 5% loss of HAL HCl after 6 months. At 40° C., composition B showed a noticeable decrease of HAL with about 1.5% loss of HAL HCl after 2 months while composition A showed a much more pronounced decrease of HAL with about 6% loss of HAL HCl. It is apparent that HAL HCl is more stable in composition B, i.e. a composition containing one or more triglycerides, than in composition A, a composition containing glycerol.

EXAMPLE 3b

Comparison of a Semi-Solid Composition According to the Invention and a Solid Pharmaceutical Composition Comprising a Solid Triglyceride Instead of a Liquid or Semi-Solid Triglyceride A solid pharmaceutical product C was prepared by melting of solid hard fat (Witepsol® H 32, Sasol, Witten) at a temperature of about 40° C. A defined quantity of HAL HCl was mixed with the molten hard fat at a temperature of about 37-39° C. The mixture was dispensed into suppository forms and was allowed to cool and solidify. White, undisrupted suppositories with a weight of 2 g were obtained. The melting point of the suppositories was determined to be 32.6° C., i.e. suitable to dissolve at human body temperature. Witepsol® H 32 is a pharmaceutical grade hard fat which is mainly comprised of triglycerides with parts of max. 15% of diglycerides and max. 1% of monoglycerides, respectively. A semi-solid pharmaceutical product D was prepared as described in Example 1 with caprylic/capric triglyceride and stearic acid as viscosity enhancer. A white ointment was obtained. Compositions C* and D* were prepared as hereinbefore described, but without any HAL HCl. Composition C* was obtained as a white, undisrupted suppositories, composition B* as a white ointment.

The numbers in the table below represent % by weight of the total product.

|  | C | C* | D | D* |
|---|---|---|---|---|
| HAL HCl | 5 | — | 5 | — |
| Miglyol ® 812 | — | — | 77 | 80 |
| Stearic acid | — | — | 18 | 20 |
| Witepsol ® H 32 | 95 | 100 | — | — |

Immediately after preparation, the compositions were visually assessed and the HAL HCl content of C and D was determined by HPCL. The freshly prepared suppositories of composition C were packed in blister packs made of PVC plastic trays and aluminum/PVC laminate. 5 g of the freshly prepared composition D were transferred into clear glass containers (3 containers per composition) with a screw lid. The blister packs and glass containers stored for 1-9 months at 5° C./ambient RH, and 25° C./60%, i.e. below the melting and drop point of the compositions. 3 samples were taken from each glass container after 1, 2, 3, 6 and 9 months and the HAL HCl content was determined by HPLC. The medium HAL HCl content was determined. In addition, the compositions were visually assessed. The compositions C* and D* were stored at the same conditions, they were visually assessed after 1, 2, 3, 6 and 9 months and they were used as a "blank" sample in the HPLC assay.

Composition C

|  | 5° C./ambient RH | | 25° C./60% RH | |
|---|---|---|---|---|
| Months | HAL (%) | Visual Assessment | HAL (%) | Visual Assessment |
| 0 | 4.90 | White, undisrupted | 4.90 | White, undisrupted |
| 1 | 5.00 | Off-white, undisrupted | 4.92 | Off-white, undisrupted |

-continued

|  | 5° C./ambient RH | | 25° C./60% RH | |
| --- | --- | --- | --- | --- |
| Months | HAL (%) | Visual Assessment | HAL (%) | Visual Assessment |
| 2 | ND | ND | ND | ND |
| 3 | 4.91 | Off-white, undisrupted | 4.74 | Off-white, undisrupted |
| 6 | 4.80 | Off-white, undisrupted | 3.84 | Off-white, undisrupted |
| 9 | 4.67 | Off-white, undisrupted | 3.56 | Off-white, undisrupted |

ND (not determined)

Composition C* was off-white at 6 month.
Composition D:

|  | 5° C./ambient RH | | 25° C./60% RH | |
| --- | --- | --- | --- | --- |
| Months | HAL (%) | Visual Assessment | HAL (%) | Visual Assessment |
| 0 | 5.15 | Off-white | 5.15 | Off-white |
| 1 | ND | ND | 5.20 | Off-white |
| 2 | 5.10 | ND | 5.05 | Off-white |
| 3 | ND | ND | ND | ND |
| 6 | ND | ND | 5.05 | Off-white |
| 9 | ND | ND | 5.30 | Off-white |

Composition D* kept an off-white appearance at all storage conditions.

While composition D was stable over a period of 9 months at 25° C., the HAL HCl concentration in composition C decreased considerably with about 3% less HAL HCl after 3 months, 23% after 6 months and 29% after 9 months. It is apparent that HAL HCl is more stable in composition D.

EXAMPLE 4

In Vivo Study of Porphyrin Build-Up in Oral Cavity

Compositions C and D were selected to study the build-up of porphyrins in vivo. The lining mucosa of the oral cavity mucosa was chosen as a model since it is a non-keratinized stratified squamous epithelium which is also found in the anal canal, the vagina and the ectocervix.

Porphyrin build-up is an indicator that the photosensitizer precursor HAL HCl was released from the composition, entered the cells and was converted to photosensitizing porphyrins.

Porphyrin build-up was measured in two healthy human volunteer subjects using a fiber point measuring device which consisted of a bundle of optical fibers connected to a spectrofluorimeter which produced the excitation light of 407 nm. The excitation light which is capable of penetrating 0.1-0.5 mm into the tissue was led through half of the fibers to the lining mucosa in the oral cavity. The resulting emission fluorescence spectrum (around 635 nm) was collected and led through the remaining fibers into a photomultiplier for quantification. Each subject received a 2 g suppository (composition C) which was placed on the lining mucosa, between the inside of the lower lip and the jaw (administration site). On another day each subject received a 2 g sample of composition D which was placed at the same administration site. Due to their respective melting points/drop points, both compositions dissolved slowly after administration. Subjects were allowed to spit out the dissolved compositions. The fluorescence spectrum at the site of administration was determined at various time points by selecting five spots within the administration area and measuring fluorescence as described above.

Figure 1:
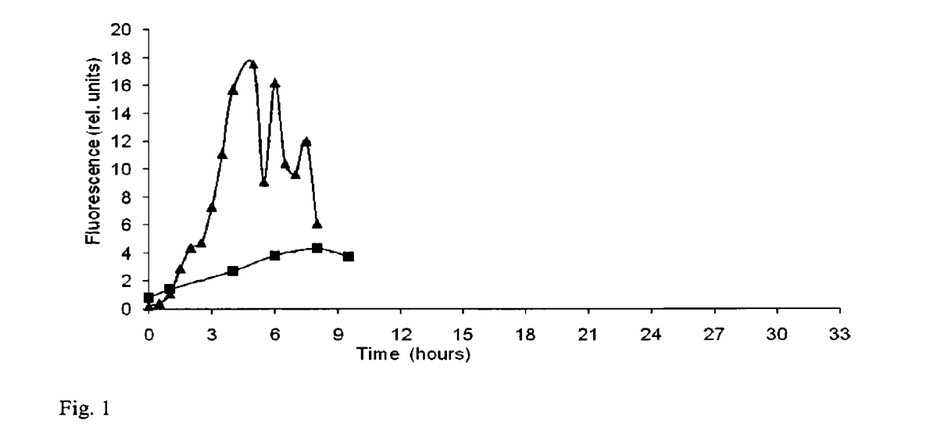
FIG. 1 displays the fluorescence over time caused by porphyrin build up in tissue of subject 1 (▲) and subject 2 (■) after administration of a solid pharmaceutical product which is not encompassed by the invention.
Figure 2:
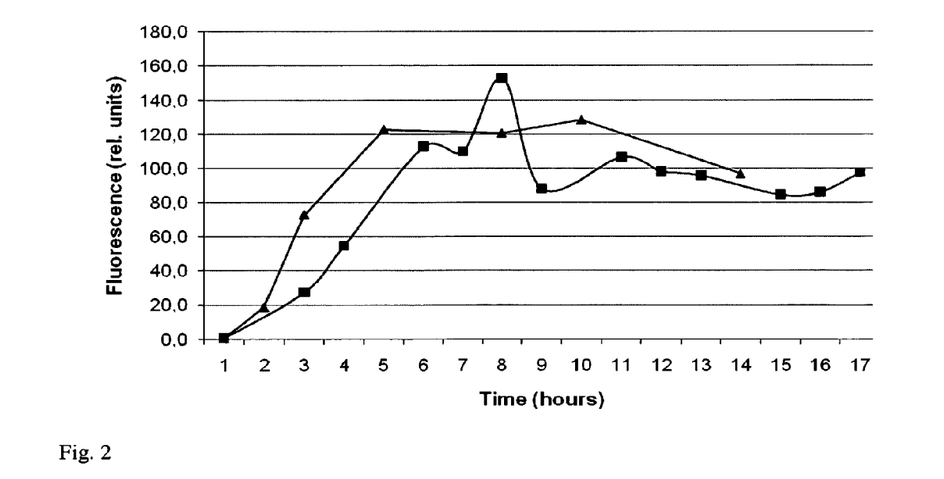
FIG. 2 displays the fluorescence over time caused by porphyrin build up in tissue of subject 1 (▲) and subject 2 (■) after administration of a semi-solid pharmaceutical product according to the invention The following examples illustrate the invention.

Baseline fluorescence was determined at the same time points at five selected spots on the underarm. The mean fluorescence and baseline fluorescence was calculated from the five spots. Fluorescence data were baseline corrected and plotted against time (FIGS. 1 and 2). FIG. 1 displays the fluorescence of composition C and FIG. 2 displays the fluorescence of composition D. It is apparent that composition D induces porphyrin build-up more efficiently then composition C.

EXAMPLE 5

In Vivo Study of Porphyrin Build-Up on the Cervix

Composition D was selected to study the porphyrins build-up in vivo on the cervix in eight healthy human female volunteer subjects.

Each subject received a 3 g sample of composition D which was applied to the ectocervix, i.e. the portion of the cervix projecting into the vagina. A FemCap, a latex-free device intended for non-hormonal contraception was placed over the ectocervix to hold the composition in place. The fluorescence spectrum at the site of administration was determined before the administration of the composition and 7 hours thereafter. Six spots within the administration area were selected for measuring fluorescence as described in Example 4. The mean and median fluorescence was calculated from the six spots for each subject and is displayed in the table below in relative units.

|  | Time 0 | | Time 7 hours | |
| --- | --- | --- | --- | --- |
|  | Mean fluorescence | Median fluorescence | Mean fluorescence | Median fluorescence |
| Subject 1 | 0.1 | 0.1 | 19.9 | 14.1 |
| Subject 2 | 0.1 | 0.1 | 55.3 | 57.8 |
| Subject 3 | 1.1 | 1.2 | 67.5 | 75.4 |
| Subject 4 | 0.4 | 0.4 | 48.4 | 48.0 |
| Subject 5 | 1.0 | 1.0 | 27.2 | 28.2 |
| Subject 6 | 0.5 | 0.3 | 43.6 | 42.3 |
| Subject 7 | 0.4 | 0.6 | 87.5 | 86.5 |
| Subject 8 | 0.4 | 0.4 | 72.9 | 71.3 |

All subjects showed a pronounced porphyrin build-up after 7 hours incubation of composition D.

What is claimed is:

1. A semi-solid composition which consists essentially of
   a) an active ingredient selected from 5-aminolevulinic acid (5-ALA) ester and pharmaceutically acceptable salts thereof; and
   b) one or more triglycerides, wherein the concentration of the one or more triglycerides is in the range of 70 to 99.5% by weight of the total weight of the composition.

2. The semi-solid composition according to claim 1 wherein said active ingredient is a compound of formula I or a pharmaceutically acceptable salt thereof $$R^2_2N-CH_2COCH_2-CH_2CO-OR^1 \quad (I)$$

wherein
   $R^1$ represents a substituted or unsubstituted alkyl group; and
   $R^2$ each represents a hydrogen atom.

3. The semi-solid composition according to claim 1 wherein the one or more triglycerides are triglycerides of glycerol and 3 identical or different $C_6$-$C_{12}$ fatty acids.

4. The semi-solid composition according to claim 1 wherein the active ingredient is 5-ALA hexyl ester or a pharmaceutically acceptable salt thereof.

5. A method of photodynamic treatment of cancer, pre-cancerous conditions and non-cancerous conditions in the female reproductive system, the anus and the penis comprising administering the semi-solid composition according to claim 1 to a patient in need of such treatment and photoactivating the active ingredient.

6. The method according to claim 5 wherein said active ingredient is a compound of formula I or a pharmaceutically acceptable salt thereof $$R^2{}_2N\text{—}CH_2COCH_2\text{—}CH_2CO\text{—}OR^1 \quad (I)$$

wherein
$R^1$ represents a substituted or unsubstituted alkyl group; and
$R^2$ each represents a hydrogen atom.

7. The method according to claim 5 wherein the one or more triglycerides are triglycerides of glycerol and 3 identical or different $C_6$-$C_{12}$ fatty acids.

8. The method according to claim 5 wherein the active ingredient is 5-ALA hexyl ester or a pharmaceutically acceptable salt thereof.

9. The method according to claim 5 wherein the semi-solid composition is contained in a drug delivery system.

10. The method according to claim 5 where said photodynamic treatment is photodynamic treatment of dysplasia or neoplasia or human papilloma virus (HPV) infections in the female reproductive system, the anus or the penis, photodynamic treatment of endometrial, cervical, vaginal, vulvar, anal or penile dysplasia or neoplasia or photodynamic treatment of HPV infections of the uterus, cervix, vagina, vulva, anus or penis.

11. The method of claim 10 where said photodynamic treatment is photodynamic treatment of cervical dysplasia, cervical neoplasia or treatment of HPV infections of the cervix.

12. The method of claim 10 where said photodynamic treatment is photodynamic treatment of cervical intraepithelial neoplasia (CIN).

13. The method of claim 10 where said photodynamic treatment is photodynamic treatment of HPV infections of the cervix.

14. A kit comprising a drug delivery system and the semi-solid composition according to claim 1.

15. The kit of claim 14 wherein said active ingredient is a compound of formula I or a pharmaceutically acceptable salt thereof $$R^2{}_2N\text{—}CH_2COCH_2\text{—}CH_2CO\text{—}OR^1 \quad (I)$$

wherein
$R^1$ represents a substituted or unsubstituted alkyl group; and
$R^2$ each represents a hydrogen atom and the one or more triglycerides are triglycerides of glycerol and 3 identical or different $C_6$-$C_{12}$ fatty acids.

16. The kit of claim 15 wherein the active ingredient is 5-ALA hexyl ester or a pharmaceutically acceptable salt thereof.

17. The kit of claim 15 wherein the active ingredient is 5-ALA hexyl ester or a pharmaceutically acceptable salt thereof.

18. A semi-solid composition which consists essentially of
a) an active ingredient selected from 5-aminolevulinic acid (5-ALA) ester and pharmaceutically acceptable salts thereof; and
b) one or more triglycerides
wherein the one or more triglycerides is a liquid triglyceride, wherein the concentration of the one or more triglycerides is in the range of 60 to 96% by weight of the total weight of the composition and which further contains c) one or more viscosity enhancers.

19. The semi-solid composition according to claim 18 wherein the one or more viscosity enhancers are selected from cellulose, carboxymethylcellulose sodium, hydroxyethylcellulose, hydroxypropyl methylcellulose, methylcellulose, synthetic polymers, vegetable gums, starch, carrageenan, agar, gelatin, wax and waxy solids.

20. The semi-solid composition according to claim 18 which consists essentially of
a) an active ingredient which is 5-ALA hexyl ester or a pharmaceutically acceptable salt thereof; and
b) a caprylic/capric triglyceride;
and which further contains stearic acid.

21. The semi-solid composition according to claim 18 which consists essentially of
a) 5% by weight of the total weight of the composition of an active ingredient which is 5-ALA hexyl ester or a pharmaceutically acceptable salt thereof; and
b) 77% by weight of the total weight of the composition caprylic/capric triglyceride;
and which further contains 18% by weight of the total weight of the composition stearic acid.

22. A method of photodynamic treatment of cancer, pre-cancerous conditions and non-cancerous conditions in the female reproductive system, the anus and the penis comprising administering the semi-solid composition according to claim 18 to a patient in need of such treatment and photoactivating the active ingredient.

23. The method according to claim 22 wherein the one or more viscosity enhancers are selected from cellulose, carboxymethylcellulose sodium, hydroxyethylcellulose, hydroxypropyl methylcellulose, methylcellulose, synthetic polymers, vegetable gums, starch, carrageenan, agar, gelatin, wax and waxy solids.

24. The method according to claim 22 wherein the semi-solid composition consists essentially of
a) an active ingredient which is 5-ALA hexyl ester or a pharmaceutically acceptable salt thereof; and
b) a caprylic/capric triglyceride;
and which further contains stearic acid.

25. The method according to claim 22 wherein the semi-solid composition consists essentially of
a) 5% by weight of the total weight of the composition of an active ingredient which is 5-ALA hexyl ester or a pharmaceutically acceptable salt thereof; and
b) 77% by weight of the total weight of the composition caprylic/capric triglyceride;
and which further contains 18% by weight of the total weight of the composition stearic acid.

26. The method according to claim 22 wherein said active ingredient is a compound of formula I or a pharmaceutically acceptable salt thereof $$R^2{}_2N\text{—}CH_2COCH_2\text{—}CH_2CO\text{—}OR^1 \quad (I)$$

wherein
$R^1$ represents a substituted or unsubstituted alkyl group; and
$R^2$ each represents a hydrogen atom.

27. The method according to claim 22 wherein the one or more triglycerides are triglycerides of glycerol and 3 identical or different $C_6$-$C_{12}$ fatty acids.

28. The method according to claim 22 wherein the active ingredient is 5-ALA hexyl ester or a pharmaceutically acceptable salt thereof.

29. The method according to claim 22 wherein the semi-solid composition is contained in a drug delivery system.

30. The method according to claim 22 where said photodynamic treatment is photodynamic treatment of dysplasia or neoplasia or human papilloma virus (HPV) infections in the female reproductive system, the anus or the penis, photodynamic treatment of endometrial, cervical, vaginal, vulvar, anal or penile dysplasia or neoplasia or photodynamic treatment of HPV infections of the uterus, cervix, vagina, vulva, anus or penis.

31. The method of claim 30 where said photodynamic treatment is photodynamic treatment of cervical dysplasia, cervical neoplasia or treatment of HPV infections of the cervix.

32. The method of claim 30 where said photodynamic treatment is photodynamic treatment of cervical intraepithelial neoplasia (CIN).

33. The method of claim 30 where said photodynamic treatment is photodynamic treatment of HPV infections of the cervix.

34. A kit comprising a drug delivery system and the semi-solid composition according to claim 18.

35. The kit of claim 34 wherein said active ingredient is a compound of formula I or a pharmaceutically acceptable salt thereof (I)

wherein
R$^1$ represents a substituted or unsubstituted alkyl group; and
R$^2$ each represents a hydrogen atom and the one or more triglycerides are triglycerides of glycerol and 3 identical or different C$_6$-C$_{12}$ fatty acids.

36. The kit of claim 34 wherein the one or more viscosity enhancers are selected from cellulose, carboxymethylcellulose sodium, hydroxyethyl cellulose, hydroxypropyl methylcellulose, methylcellulose, synthetic polymers, vegetable gums, starch, carrageenan, agar, gelatin, wax and waxy solids.

37. The kit of claim 34 wherein the semi-solid composition consists essentially of
  a) an active ingredient which is 5-ALA hexyl ester or a pharmaceutically acceptable salt thereof; and
  b) a caprylic/capric triglyceride;
  and which further contains stearic acid.

38. The kit of claim 34 wherein the semi-solid composition consists essentially of
  a) 5% by weight of the total weight of the composition of an active ingredient which is 5-ALA hexyl ester or a pharmaceutically acceptable salt thereof; and
  b) 77% by weight of the total weight of the composition caprylic/capric triglyceride;
  and which further contains 18% by weight of the total weight of the composition stearic acid.

39. The semi-solid composition according to claim 18 wherein the active ingredient is 5-ALA hexyl ester or a pharmaceutically acceptable salt thereof.

* * * * *